United States Patent [19]

Cole

[11] Patent Number: 5,356,817
[45] Date of Patent: Oct. 18, 1994

[54] METHODS FOR DETECTING THE ONSET, PROGRESSION AND REGRESSION OF GYNECOLOGIC CANCERS

[75] Inventor: Laurence A. Cole, Hamden, Conn.

[73] Assignee: Yale University, New Haven, Conn.

[21] Appl. No.: 645,308

[22] Filed: Jan. 24, 1991

Related U.S. Application Data

[63] Continuation of Ser. No. 204,447, Jun. 9, 1988, abandoned.

[51] Int. Cl.$^5$ .............................................. G01N 33/00
[52] U.S. Cl. ...................................... 436/64; 436/813; 436/510
[58] Field of Search ................................. 436/63–65, 436/813, 814, 818, 510–511; 424/1.1, 100

[56] References Cited

U.S. PATENT DOCUMENTS

| | | | |
|---|---|---|---|
| 4,116,776 | 9/1978 | Dalbow et al. | 436/519 |
| 4,123,224 | 10/1978 | Givner et al. | 436/510 |
| 4,144,031 | 3/1979 | Acevedo et al. | 436/519 |
| 4,310,455 | 1/1982 | Bahl | 436/510 |
| 4,387,166 | 6/1983 | Maes | 436/813 |
| 4,489,166 | 12/1984 | Joshi | 436/510 |
| 4,514,505 | 4/1985 | Canfield et al. | 436/500 |
| 4,804,626 | 2/1989 | Bellet et al. | 436/818 |

OTHER PUBLICATIONS

Cole et al. "Urinary Gonadotropin Fragment (UGF) Measurements in the Diagnosis and Management of Ovarian Cancer", The Yale Journal of Biology and Medicine 62 (1989), 367–378.

Sheth, N. A. et al, "Inappropriate Secretion of Human Placental Lactogen and β-Subunit of hCG by Cancer of the Uterine Cervix", Gynecol Oncol 11 (3), 1981, Cancer Research Inst., Parel, Bombay, India.

Papapetrou, P. D. and Nicopoulou, S. C., The Origin of a Human Chorionic Gonadotropin Beta-Subunit Core Fragment in the Urine of Patients with Cancer, A. Endocrinologica, 112, 415–422 (1986).

Cole, L. A., Wang, Y., Elliott, M., Latif, M., Chambers, J. T., Chambers, S. K. and Schwartz, P. E., Urinary Human Chorionic Gonadotropin Free Beta-Subunit and Beta-Core Fragment: A New Marker of Gynecologic Cancers, Cancer Res., 48, 1356–1360 (1988).

1987 Asco Abstract.

Wehmann, R. E. and Nisula, B. C., Metobolic Clearance Rates of the Subunits of Human Chorionic Gonadotropin in Man, J. Clin. Endocrinol. Metab., 48, 753–759 (1979).

R. O. Hussa, Human Chorionic Gonadotropin, A Clinical Marker: Review of its Biosynthesis, Ligand Rev., 3, 1–43 (1981).

Wang, Y., Schwartz, P. E. and Cole, L. A., Serum hCG Investigation in Patients with Non-Trophoblastic Cancer, J. Obstet. Gynecol. China, (no date provided).

Birken, S., Armstrong, E. G., Kolks, M. A. G., Cole, L. A., Agosto, G. M., Krichevsky, A. and Canfiled, R. E., The Structure of the Human Chorionic Gonadotropin Beta Core Fragment from Pregnancy Urine, Endocrinology, vol. 123, No. 1, 572–583 (No date provided).

Schroeder, H. R. and Halter, C. M., Specificity of Human Beta-Choriogonadotropin Assays for the Hormone and for an Immunoreactive Fragment Present in (List continued on next page.)

Primary Examiner—Lyle A. Alexander
Attorney, Agent, or Firm—Frishauf, Holtz, Goodman & Woodward

[57] ABSTRACT

A method for detecting the progression or regression of a gynecologic cancer in a female by:
(a) taking a first measurement of the amount of human chorionic gonadotropin beta-subunit core fragment in a bodily non-blood fluid sample from a female known to be suffering from a gynecologic cancer,
(b) subsequent to step (a), taking one or more further measurements of human chorionic gonadotropin beta-subunit core fragment from a bodily non-blood fluid sample from the female,
(c) comparing the first measurement to said one or more further measurements to ascertain if the human chorionic gonadotropin beta-subunit core fragment is increasing or decreasing, as an indication that the cancer is respectively progressing or regressing.

9 Claims, 3 Drawing Sheets

OTHER PUBLICATIONS

Urine During Normal Pregnancy, Clin. Chem., 29, 667–671 (1983).

Lefort, G. P., Stolk, J. M. and Nisula, B. C., Renal Metobolism of the Beta–Subunit of Human Choriogonadotropin in the Rat, Endocrinology, 119, 924–931 (1986).

Cole, L. A., Kroll, T. G., Ruddon, R. W. and Hussa, R. O., Differential Occurrence of Free B and Free A Subunits of Human Chorionic Gonadotropin in Pregnancy Sera, J. Clin. Endocrinol. Metab., 58, 1200–1202 (1984).

Cole, L. A., Occurrence and Properties of Glycoprotein Hormone Free Subunits, in Microheterogeneity of Glycoprotein Hormones (H. Grotjan and B. Keel, Eds.), CRC Press, New York, (No date provided).

Cole, L. A., Hartle, R. J., Laferla, J. J. and Ruddon, R. W., Detection of the Free Beta–Subunit of Human Chorionic Gonadotropin in Cultures of Normal and Malignant Trophoblast Cells, Pregnancy Sera, and Sera of Patients with Choriocarcinoma, Endocrinology, 113, 1176–1178 (1983).

Atack, D. B., Nisker, J. A., Allen, H. H., Tustanoff, E. R. and Levin, L., CA 125 Surveillance and Second–Look Laparotomy in Ovarian Carcinoma, Am. J. Obstet. Gynecol., 154, 287–289 (1986).

Schwartz, P. E., Chambers, S. K., Chambers, J. T., Gutmann, J., Katopodis, N. and Foemmel, R. S., Circulating Tumor Markers in the Monitoring of Gynecologic Malignancies, Cancer, 60, 353–361 (1987).

Alvarez, R. D., To, A., Boots, L. R., Shingleton, H. M., Hatch, K. D., Hubbard, J., Soong, S. J. and Potter, M. E., CA 125 as a Serum Marker for Poor Prognosis in Ovarian Malignancies, Gynecol. Oncol., 26, 284–289 (1987).

E. Silverberg, Cancer Statistics, CA–A Cancer J. Clinicians, 6, 9–26 (1986).

Schwartz, P. E., Gynecologic Cancer, In J. A. Spittle, Jr. (ed.), Clinical Medicine, pp. 1–44. Philadelphia: Harper and Row, (1986).

Bast, R. C., Kung, T. L., St. John, E., Jenison, E., Niloff, J. M., Lazarus, H., Berkowitz, R., Leavitt, T., Griffiths, T., Parker, L., Zurawaski, V. R. and Knapp, R. C., A Radioimmunoassay Using a Monoclonal Antibody to Monitor the Course of Epithelial Ovarian Cancer, N. Engl. J. Med., 309, 883–887 (1983).

Masure, H. R., et al, "Charac. of a Small Molec. Siz Urin. Immunoreactive Human Chorionic Gonado. (hcG)–Like Substance Produced by Normal Placenta and by hCG–Secreting Neoplasms", *J. of Clin. Endocrin. & Metab.,* 53, No. 5, pp. 1014–1020 (no date provided).

Seski, J., et al, "Chemotherapy for Endometrial Cancer", Annual Clinical Conf. on Cancer, vol. 29, pp. 327–334 (no date provided).

Yajima, A., et al, "Effect of Cytologic Screening on the Detection of Cer. Carcinoma", *Obst. & Gyn.,* vol. 59, No. 5, Sep. 28, 1981.

Jordan, S., et al, "The Significance of Cerv. Cytologic Dysplasia", *Acta. Cytologica,* 0001–5547/81/25–03–0237/pp. 2347–244 (no date provided).

Schwartz, P. E., et al, "Eval. of Squamous Cell Carcin. Antigen (SCC) and Lipid–Assoc. Sialic Acid (LSA) in Monitoring Patients w/Cerv. Cancer", *Proceedings of ASCO,* 6, Gynecological Tumors, Mar. 1987, #445.

METHODS FOR DETECTING THE ONSET, PROGRESSION AND REGRESSION OF GYNECOLOGIC CANCERS

GOVERNMENT RIGHTS

This invention was made with United States government support under Grant CA44131 from the National Cancer Institute. The United States Government has certain rights in this invention.

This application is a continuation of application Ser. No. 204,447, filed Jun. 9, 1988 now abandoned.

BACKGROUND OF THE INVENTION

1. Field of the Invention

The present invention concerns non-invasive methods for detecting the onset, progression and regression of gynecologic cancers. More particularly, the present invention relates to the detection of human chorionic gonadotropin beta-subunit core fragment as a marker of gynecologic cancers.

2. Background Information

Cervical cancer is one of the most common malignancies afflicting women (E. Silverberg, "Cancer Statistics", *CA-A Cancer J. Clinicians,* 6, 9–26, (1986)). The Pap (Papanicolaou) smear has led to early diagnosis and has mainly been responsible for the overall improvement in survival reported for this disease (Yajima, A., Mori, T., Sato, S , Wakisaka, T , and Suzuki, M., "Effect of Cytologic Screening on the Detection of Cervical Carcinoma", *Obstet. Gynecol.,* 59, 565–568 (1982). However, patients who are not able or do not wish to undergo Pap smear (an invasive method) screening run the risk of unsuccessful treatment if they wait for symptoms (pain, bleeding and/or discharge) to develop. This often is the situation with women who are in epidemiologic groups at highest risk for developing cervical cancer. For example, the National Cancer Institute of Peru recently reported that 80% of 1,100 new cervix cancer patients seen annually have stage III or IV disease. Routine Pap Smear screening is not accepted by these patients and the survival is extremely poor (Castellano, C., "Manejo Del Paciente Con Citologia Anormal", Ninth Congress, Cancer in Peru, Lima, (1985)).

The Pap smear as a screening technique for cervical cancers, however, can be inaccurate. False negative rates for Pap smears vary greatly from 12.5% to 45% (C. Castellano, supra; Jordan, S. W., Smith N. L., and Dike, L. S., "The Significance of Cervical Cytologic Dysplasia", *Acta Cytol.,* 25, 237–244, (1981)) .

Among American women, the ovary is the second most common site of gynecologic cancer (E. Silverberg, supra). The common epithelial ovarian cancers lack early warning symptoms and there are no routine tests, like the Pap smear, for early detection. Ovarian cancer is usually not suspected until a pelvic mass is present and, if not detected until advanced stage, is almost always fatal (Schwartz, P. E., "Gynecologic Cancer" In: J. A., Spittle, Jr. (ed.), *Clinical Medicine,* pp. 1–44. Philadelphia: Harper and Row, (1985)).

A readily available urine test that would aid in the detection of women at increased risk for having gynecologic malignancies, particularly cervix and ovarian cancer would be a major step forward for patients in whom advanced stage disease is almost always fatal. Such a test may obviate the need among those with religious or ethical concerns for an unacceptable pelvic examination and Pap smear.

The efficacy of treatment for patients with recurrent gynecologic cancer is reflected in the volume of cancer at the time recurrence is documented and the sites of recurrent disease. Therapy may be of limited value when recurrent disease is not identified until the patient has clinical signs or symptoms. Early recognition of occult persistent or recurrent cancer may lead to more effective therapeutic intervention.

Surgical intervention in the form of radical surgery may cure patients with central recurrence of cervical cancer. Diagnosis of persistent or recurrent central disease in a radiation field may be difficult to confirm by cytologic or biopsy techniques. An accurate tumor marker for cervical cancer may lead to earlier recognition and more rapid diagnosis and treatment.

Previous experience suggested a role for lipid-associated sialic acid (LASA) in this regard, but not for squamous cell carcinoma antigen (SCC) (Schwartz, P. E., Foemmel, R. S., Chambers, S. K., and Chambers, J. T., "Evaluation of Squamous Cell Carcinoma Antigen (SCC) and Lipid-association Sialic Acid (LSA) in Monitoring Patients With Cervical Cancer", *Proc. Am. Soc. Clin. Oncol.,* 6, 113 (1987)).

Early recognition of recurrent or persistent endometrial cancer may lead to more rapid treatment with potentially more effective combination chemotherapy (Seski, J. C., Kasper, G. L., and Kunschner, A. J., "Chemotherapy for Endometrial Cancer, in Diagnosis and Treatment Strategies" (F. N. Rutledge, R. S. Freedman and D. M. Gershenson Eds.), University of Texas Press, Austin, pp. 327–334 (1987)).

Multiple circulating markers have been evaluated in the management of epithelial ovarian cancer patients, the most promising of which is CA 125 (Bast, R. C., Kung, T. L., St. John, E., Jenison, E., Niloff, J. M., Lazarus, H., Berkowitz, R., Leavitt, T., Griffiths, T., Parker, L., Zurawski, V. R., and Knapp, R. C., "A Radioimmunoassay Using a Monoclonal Antibody to Monitor the Course of Epithelial Ovarian Cancer", *N. Engl. J. Med.,* 309, 883–887 (1983)).

As high as eighty percent of patients with non-mucinous ovarian cancers can have elevated levels of CA 125 in their serum, which will become nondetectable as the cancer responds to treatment. Unfortunately, in a recently reported clinical trial using CA 125 in the management of ovarian cancer, 6 of 11 (55%) patients who were clinically free of disease and had CA 125 levels that were in the normal range, were found to have persistent cancer at a second-look procedure (Atack, D. B., Nisker, J. A., Allen, H. H., Tustanoff, E. R., and Levin, L., "CA 125 Surveillance and Second-look Laparotomy in Ovarian Carcinoma", *Am. J. Obstet. Gynecol.,* 154, 287–289 (1986)).

Similarly, at Yale-New Haven Hospital the published false-negative rate for CA 125 (cut-off 35 U/ml) at second-look surgery is 40% (Schwartz, P. E., Chambers, S. K., Chambers, J. T., Gutmann, J., Katopodis, N., and Foemmel, R. S., "Circulating Tumor Markers in the Monitoring of Gynecologic Malignancies", *Cancer* 60, 353–361 (1987) Other early clinical trials have shown that decreasing CA 125 levels in ovarian cancer patients are not necessarily an indicator of regressive disease (Alvarez, R. D., To, A., Boots, L. R., Shingleton, H. M., Hatch, K. D., Hubbard, J., Soong, S. J., and Potter, M. E., "CA 125 as a Serum Marker for Poor Prognosis in Ovarian Malignancies", *Gynecol. Oncol.*, 26, 284–309, (1987)).

Once the diagnosis of ovarian cancer is established the currently available clinical markers tend to parallel clinical examination findings, but do not guarantee the efficacy of the treatment in those patients who are clinically free of disease, nor are they sufficiently sensitive to avoid the use of second-look operations.

Human chorionic gonadotropin (hCG) is a glycoprotein hormone composed of the following two dissimilar subunits: alpha 92 amino acids long and beta 145 amino acids long, joined non-covalently. It is normally produced by trophoblast tissue and can be detected in the blood and urine of women in pregnancy or trophoblast disease. Free forms of hCG alpha and beta subunits, which can account for as much as 90% of the total produced, are also found in blood and urine in pregnancy and trophoblast disease (Cole, L. A., Kroll, T. G., Ruddon, R. W., and Hussa, R. O., "Differential Occurrence of Free B and Free A Subunits of Human Chorionic Gonadotropin in Pregnancy Sera", *J. Clin Endocrinol. Metab.*, 58, 1200–1202 (1984); Cole, L. A., "Occurrence and Properties of Glycoprotein Hormone Free Subunits", in *Microheterogeneity of Glycoprotein Hormones* (H. Grotjan and B. Keel, Eds.), CRC Press, New York, in press; Cole, L. A., Hartle, R. J., Laferla, J. J., and Ruddon, R. W., "Detection of the Free beta-subunit of Human Chorionic Gonadotropin In Cultures of Normal and Malignant Trophoblast Cells, Pregnancy Sera, and Sera of Patients with Choriocarcinoma", *Endocrinology*, 113, 1176–1178 (1983)

Numerous researchers have shown that human chorionic gonadotropin is present in the circulation of approximately 20% of women with cancer. Because of the low percentage positive for cancer it has not been used as a marker for gynecological cancer.

Free beta-subunit missing sialic acid residues on its carbohydrate moieties (asialo free beta), and fragmented asialo free beta (core fragment) composed of residues 6–40 disulfide-linked to 55–92, are also produced in pregnancy and trophoblast disease (Birken, S. , Armstrong, E. G., Kolks, M. A. G., Cole, L. A., Agosto, G. M., Krichevsky, A., and Canfield, R. E., "The Structure of the Human Chorionic Gonadotropin beta Core Fragment from Pregnancy Urine", *Endocrinology*, in press.) .

Free beta-subunit, asialo free beta and the core fragment of asialo beta-subunit, together called UGF, are rapidly cleared from the circulation and are more readily detected in urine than in serum samples (Schroeder, H. R., and Halter, C. M., "Specificity of Human beta-Choriogonadotropin Assays for the Hormone and for an Immunoreactive Fragment Present in Urine During Normal Pregnancy", *Clin. Chem.*, 29, 667–671 (1983); Lefort, G. P., Stolk, J. M., and Nisula, B. C., "Renal Metobolism of the beta-subunit of Human Choriogonadotropin in the Rat", *Endocrinology*, 119, 924–931 (1986); Wehmann, R. E., and Nisula, B. C., "Metobolic Clearance Rates of the Subunits of Human Chorionic Gonadotropin in Man", *J. Clin. Endocrinol. Metab.*, 48, 753–759 (1979)) .

Ectopic hCG has been detected in the blood and tissues of patients with non-trophoblastic cancers, most notably gynecologic malignancies (R. O. Hussa, "Human Chorionic Gonadotropin, a Clinical Marker: Review of its Biosynthesis", *Ligand Rev.*, 3, 1–43, (1981))

In a recent compilation of 38 separate studies (n=692), 36% of women with cervical, 27% of those with endometrial and 13% of those with vulvar cancers were shown to have detectable levels of hCG in radioimmunoassays. This low percentage with detectable levels and the associated low titers have, however, restricted the use of hCG in detecting and following the therapy of gynecologic cancers (Hussa, supra). In studies of women with gynecologic cancer, using the Hybritech "Tandem" hCG-specific immunoradiometric assay (<0.1% hLH and free subunit crossreactivity), it was found that only 11 of 64 (17%) had detectable (>0.2 ng/ml, equivalent of >2.0 mIU/ml) serum levels of hCG (Wang, Y., Schwartz, P. E., Cole, L. A., "Serum hCG Investigation in Patients with Non-trophoblastic Cancer", *J. Obstet. Gynecol. China*, in press). The average level was found to be just 0.30 ng/ml (equivalent of 3 mIU/ml). Serial serum samples from 14 cancer patients with elevated hCG levels were examined. Levels were measured at the start and following therapy. Strangely, in 8 of 10 women with progressive cancer and increasing tumor mass hCG levels went down (Wang et al, supra). Furthermore, in 4 of 4 women with regressing disease and diminution of tumor mass, hCG levels went up. Clearly, serum hCG has very limited value in screening and in the management of patients with gynecologic cancer.

hCG free beta-subunit and core fragment, UGF, have also been detected in patients with non-trophoblastic cancers (Papapetrou, P. D., and Nicopoulou, S. C., "The Origin of a Human Chorionic Gonadotropin beta-subunit Core Fragment in the Urine of Patients with Cancer", *a Endocrinologica*, 112, 415–422 (1986); Vaitukaitis, J. L., "Characterization of a Small Molecular Size Urinary Immunoreactive Human Chorionic Gonadotropin (hCG)-like Substance Produced by Normal Placenta and by hCG-secreting Neoplasms", *J. Clin. Endocrinol. Metab.*, 53, 1014–20 (1981)) .

In patients with UGF in urine, the fact that it originates from the cancer tissue itself has been established by the finding of significant levels (average 1.0 ng/mg protein) in 5 of 5 tumor tissue homogenates. In a preliminary study of UGF in patient urines (Cole, L. A., Wang, Y., Elliott, M., Latif, M., Chambers, J. T., Chambers, S. K., and Schwartz, P. E., "Urinary Human Chorionic Gonadotropin Free beta-Subunit and beta-Core Fragment: A New Marker of Gynecologic Cancers, *Cancer Res.*, 48, 1356–1360, (1988)) levels were measured in spot samples from 50 healthy women and from 68 patients with active gynecologic cancer. Elevated levels (>0.2 ng/ml beta-subunit, or molar equivalent of the beta core fragment) were detected in 3 of the control and 50 of the cancer samples. Although adjustments were not made for urine concentration (creatinine level), a sensitivity of 74 % and a specificity of 94% of UGF for gynecologic cancers was suggested. These preliminary findings showed that gynecologic cancers more commonly produce free-subunits or beta core fragment, than hCG, and that the use of UGF as a tumor marker warranted further investigation.

SUMMARY OF THE INVENTION

It is an object of the present invention to provide non-evasive methods to detect the onset and progression of gynecologic cancers. This object, as well as other objects, advantages and aims is satisfied by the present invention.

The present invention concerns a method for detecting the progression of a gynecologic cancer in a female comprising
(a) taking a first measurement of the amount of human chorionic gonadotropin beta-subunit core fragment in a bodily non-blood fluid sample from a female known to be suffering from a gynecologic cancer,
(b) subsequent to step (a), taking one or more further measurements of human chorionic gonadotropin beta-subunit core fragment from a bodily non-blood fluid sample from said female, and
(c) comparing the first measurement to said one or more further measurements to ascertain if the humor chorionic gonadotropin beta-subunit core fragment is increasing or decreasing, as an indication that the cancer is respectively, progressing or regressing.

The present invention is also directed to a method for detecting the presence of a gynecologic cancer in a female comprising assaying a bodily non-blood fluid sample from a female and determining if said sample contains human chorionic gonadotropin beta-subunit core fragment, the presence of which is an indication of a gynecologic cancer.

The present invention further relates to a method for detecting the presence of a gynecologic cancer in a female comprising
(a) assaying a plasma or tissue sample from a female for the presence of CA 125, and at or about the same time
(b) assaying a bodily non-blood sample, e.g., a urine or tissue sample from the female for the presence of human chorionic gonadotropin beta-subunit core fragment.

The present invention is still further directed to a kit for detecting the onset or progression of gynecologic cancer. Such kit containing in one or more containers, a means for detecting human chorionic gonadotripin beta-subunit core fragment. In a preferred embodiment, such kit will also contain a means to detect CA 125.

DETAILED DESCRIPTION OF THE INVENTION

Description of Preferred Embodiments

The present invention concerns methods for detecting the onset, progression and regression of gynecologic cancers e.g., cervical cancer, ovarian cancer, endometrial cancer, uterine cancer, and vulva cancer, in human females. The gist of the invention lies in the detection and determination of human chorionic gonadotropin beta-subunit core fragment as a marker for gynecologic cancers.

The methods of the invention encompass assaying for human chorionic gonadrotropin beta-subunit core fragment in non-blood human bodily fluid samples from human females, e.g., urine, ascites fluid, spinal fluid, biopsy material, surgical samples, saliva and vaginal fluid. Preferably the assays are conducted on urine samples.

Although the present invention can be used to detect gynecologic cancers, it is believed that the preferred use of the present invention would be to periodically check the level of human chorionic gonadrotropin beta-subunit core fragment in women known to have gynecologic cancer and who have received treatment, e.g., surgery and/or chemotherapy. Thus, following such therapy, women patients will be tested for the amount of human chorionic gonadotropin beta-subunit core fragment in their urine as a measure of the efficacy of the therapy. An increase in human chorionic gondatropin beta-subunit core fragment will generally mean a recurrence of the cancer, whereas no increase or a decrease will generally mean a regression, indicating that the therapy is working. Alternatively, the level of gonadotropin beta-subunit core fragment will be measured before therapy, if level fails to go down following chemotherapy or radiotherapy, it would suggest resistance and the need for alernate treatment. If levels start to rise in the months after successful therapy, it would be an early signal of recurrence.

Conventional assay techniques can be used to detect and quantify amounts of gonadotropin beta-subunit core fragment. An example of one assay would involve determining the levels of hCG, beta fragment and beta-subunit and then testing for the C-terminal peptide (which is not present on the fragment). UGF, hCG free beta-subunit, asialo free beta-subunit and a core fragment, are secreted into the circulation by gynecologic malignancies, and are rapidly cleared.

A preferred assay, however, involves the use of a monoclonal antibody that recognizes any of hCG, beta-fragment or beta-subunit.

Kits for conducting the methods of the present invention would comprise in one or more containers, a means for detecting human chorionic gonadrotropin beta-subunit core fragment, e.g., a monoclonal antibody which reacts with human chorionic gonadrotropin beta-subunit core fragment labeled with any convenient label, e.g., a radiolabel or an enzyme.

In a preferred kit according to the present invention, means, e.g., monoclonal antibodies, to detect each of human chorionic gonadrotropin beta-subunit core fragment and CA 125 will be provided.

SUMMARY OF RESULTS

In a control group (Table 1 hereinbelow), the average level of UGF was found to be 0.13 ng/ml. Selecting a cut-off value of 0.2 ng/ml, 6 false positives were detected among 67 samples. Using the same cut-off, 72 true positives were detected among 112 women with active gynecologic cancer providing spot urines. While the average UGF level was 1.8 ng/ml in the cancer patients, it averaged <0.5 ng/ml in the 6 of 67 positive control samples. A higher sensitivity was observed for ovarian vs. endomertrial and cervical cancer (70% vs. 59% and 59%). This, however, was shown to be related to the more advanced disease in the ovarian cancer group, and an overall 64% sensitivity was proposed (Table 2 hereinbelow). When samples were restricted to first morning urines (mean creatinine level 1.0 ng/ml), or to other sample where creatinine level confirmed as >0.5 mg/ml, the overall sensitivity of UGF was raised to 76% (Table 3 hereinbelow), which exceeded that of LASA and CA 125 for all gynecologic cancers. Positive UGF levels were found in 73% of cervical (vs. LASA in 32%), 65% of endometrial (vs. CA 125 in 61%) and 83% of ovarian (vs. CA 125 in 65%) cancer patients. Measurement of both LASA and UGF or CA 125 and UGF did not improve upon the sensitivity of UGF alone for cervical or endometrial cancer, however, detection of positive UGF (morning urine) or CA 125 in the same patient raised the sensitivity for ovarian cancer to 92%. UGF were elevated (> 0.2 ng/ml) in 4 of 5 patients with serous ovarian cancer having normal-range (<35 U/ml) CA 125 levels.

The specificity of UGF (morning or >0.5 mg/ml creatinine) using a cut-off of 0.2 ng/ml was found to be 89%. The specificity, however, can be raised to 96% by using a cut-off of 0.5 ng/ml. Although the sensitivity dropped from 76% to 63% by raising the cut-off limit, the very-high specificity and associated positive predictive value (94%), make this appropriate for a relatively simple cancer-screening urine test.

Overall, UGF levels correlated with clinical status in 23 of the 28 patients (82%). Four of the 5 patients with non-correlation UGF levels had values consistently in the normal range (<0.2 ng/ml). The remaining patient with discordant UGF level and clinical status (Patient 15) was unusual in that the urine was negative for UGF (<0.2 ng/ml) on first visit, with a stage III ovarian cancer, yet low positive (0.5 ng/ml) post-surgery when she was clinically free of disease. Summarizing, 23 of 24 women with an elevated UGF level during the study period had levels concordant with their clinical status.

Figure 1:
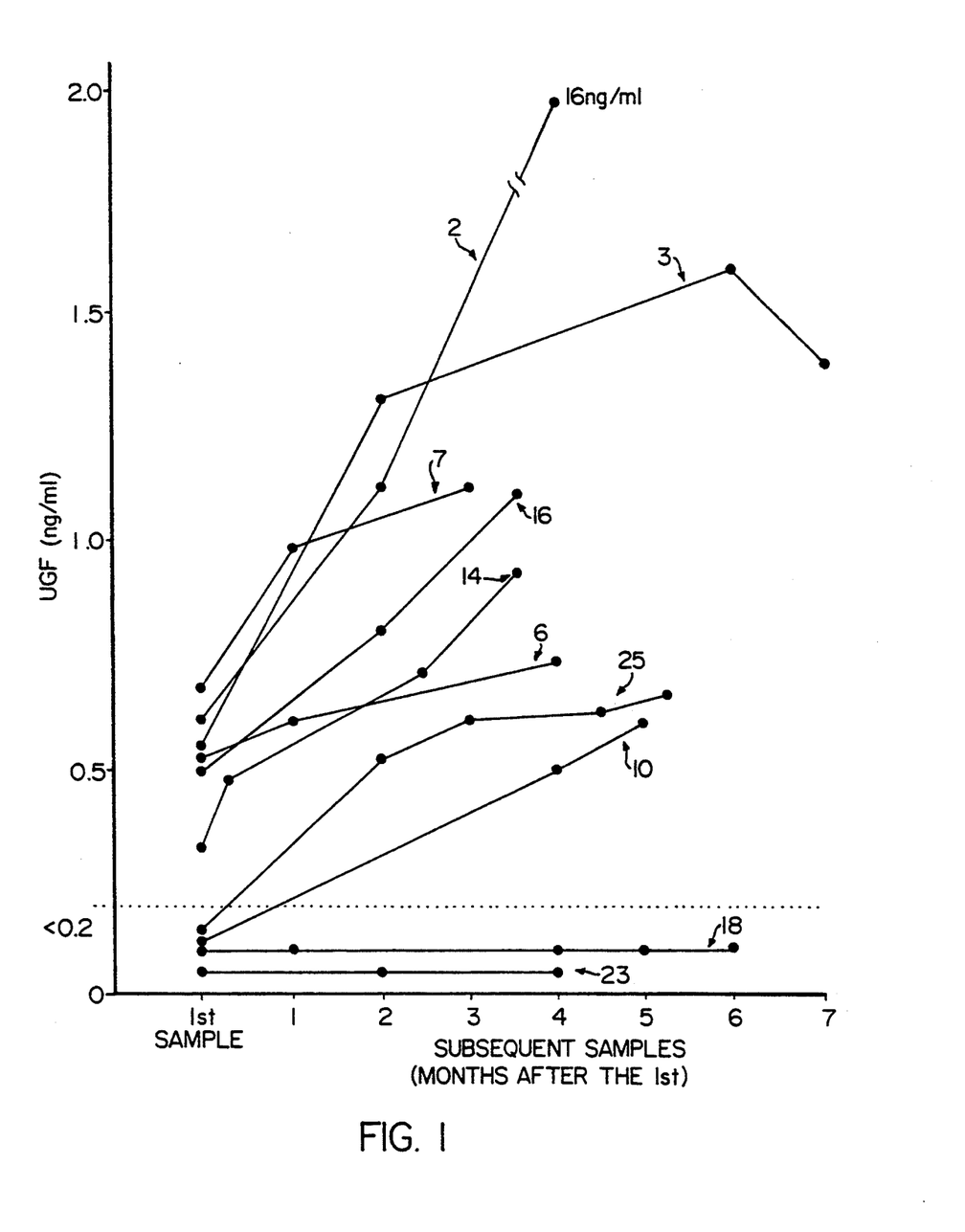
FIG. 1 is a plot depicting UGF levels in women undergoing therapy for gynecologic cancer. Values are from women with a regressive course or diminishing tumor mass. The patient number, beside each line, references the clinical evaluations in Table 5 hereinbelow.
Figure 2:
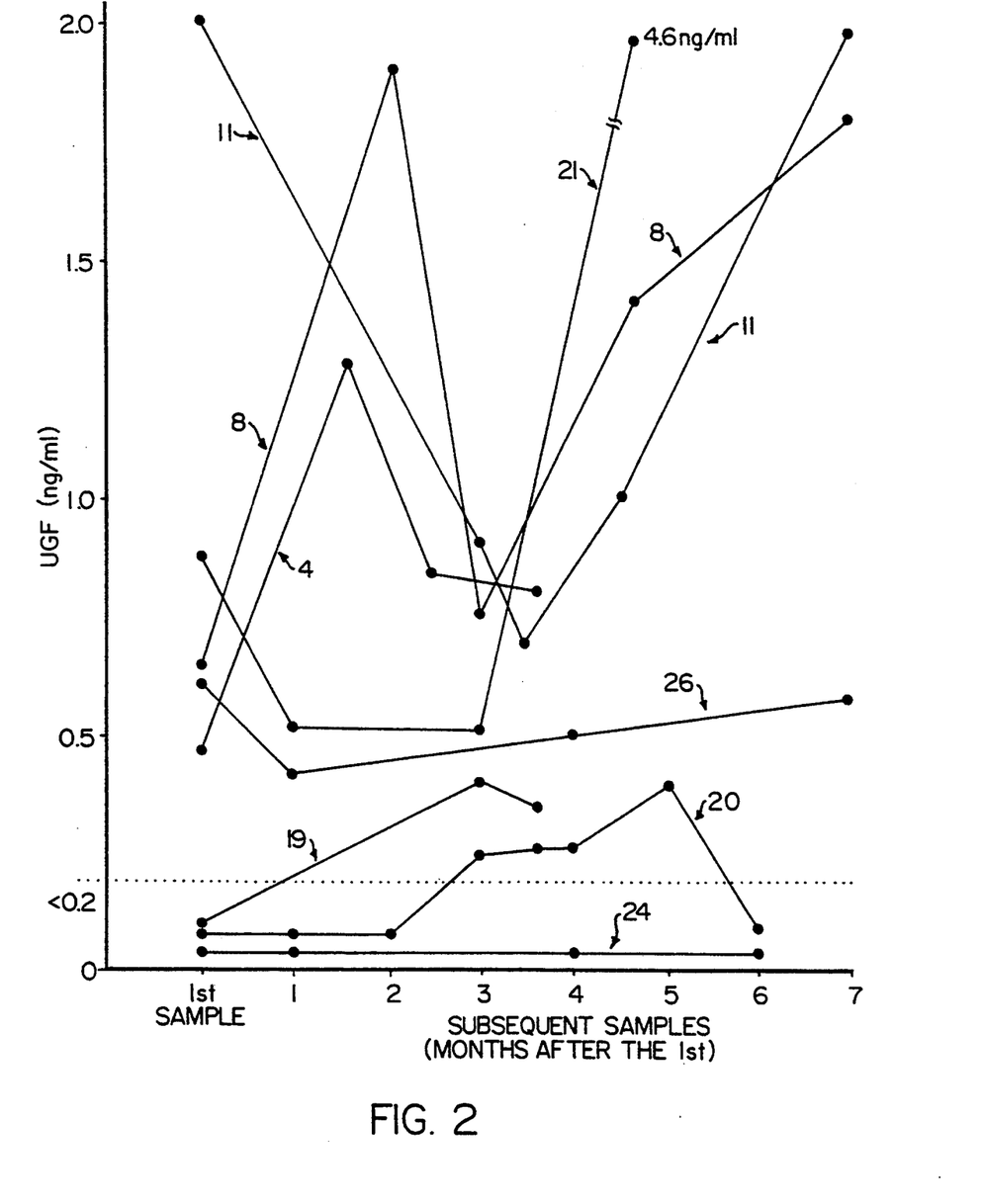
FIG. 2 is a plot depicting UGF levels in women undergoing therapy for gynecologic cancer. Values are from 10 women with a progressive course or increasing tumor mass. The patient number, beside each line, references the clinical evaluations in Table 5.

The 23 of 28 women with UGF levels correlating with clinical course comprised 2 of 3 with cervical, 8 of 8 with endometrial, and 13 of 17 with ovarian malignancy. Correlation of UGF levels and clinical status was observed in 8 of the 10 patients with successful therapy and continuously diminishing tumor mass (FIG. 1), and in 8 of 10 with progressive disease (FIG. 2). These results show that UGF can be used in monitoring all the common gynecologic cancers, and suggest similar efficacy in following advancing and diminishing disease.

The utility of UGF in monitoring patients with gynecologic cancers was compared with that of CA 125 and LASA (Table 5). Changes in clinical course were accurately followed by CA 125 levels in 59%, by LASA in 35%, compared with by UGF in 82% of these with gynecologic cancer. CA 125 levels correlated with clinical course in 10 of 14 patients with serous ovarian cancer, as did UGF. CA 125 levels, however, were concordant only with clinical course in 1 of 3 patients with non-serous disease, compared with 3 of 3 for UGF. interestingly, UGF was effective in monitoring therapy in most of the patients with negative (<35 U/ml) or non-correlating CA 125 levels. Using both CA 125 and UGF, levels of one or both markers correlated with clinical course in 2 of 3 patients with cervical, 8 of 8 patients with endometrial and 16 of 17 patients with ovarian cancer. Effectively, either CA 125 or UGF accurately monitored the course of therapy in 26 of 28 patients with gynecologic cancer (93%). Patient 20 (Table 5 and FIG. 3) was treated for serous ovarian cancer, and during the study period had no clinical evidence of disease and normal-range CA 125 levels. However, consistently elevated UGF levels were detected. Second-look surgery revealed multiple occult intraperitoneal metastases. Following surgery the UGF level dropped to the normal range. This illustrates the potential efficacy of UGF in detecting cancer in patients with no evidence of disease. These results and the demonstration that UGF levels are detected in 4 of 5 patient with active serious ovarian cancer and normal-range CA 125 levels, indicated that UGF may identify many ovarian cancer patients for whom CA 125 is an ineffective biomarker.

Examples

Example 1: The Sensitivity and Specificity of UGF for Gynecologic Cancers and the Effects of Urine Concentration (Creatinine Levels) on Sensitivity and Specificity; Comparisons Against CA 125 and Lipid-Associated Sialic Acid (LASA)

Patients p Blood and urine samples were collected from female patients with active gynecological cancer. Control serum and urine samples were collected from healthy subjects with no history of neoplasia, from woman previously-treated for intraepithelial neoplasia and from those with non-neoplastic disorders. A breakdown of control and cancer patient characteristics is presented in Table 1 hereinbelow:

TABLE 1

| Control and Cancer Patient Characteristics | |
|---|---|
| Control Urines | |
| Women, non-pregnant, previously treated for intraepithelial neoplasia, or having a non-neoplastic gynecologic disorder | 10 |
| Women, non-pregnant, with no evidence of disease or history of neoplasia | 57 |
| Total urine samples | 67 |
| Control Serum | |
| Women, non-pregnant, previously treated for intraepithelial neoplasia, or having a non-neoplastic gynecologic disorder | 58 |
| Women, non-pregnant, with no evidence of disease or history of neoplasia | 12 |
| Total serum samples | 70 |

Cancer Serum and Urines

Parallel samples from women with proven malignancy on first visit to a gynecology oncology clinic:

| | |
|---|---|
| Cervix, invasive squamous carcinoma | 26 |
| Cervix, invasive adenocarcinoma | 6 |
| Endometrium, adenocarcinoma | 23 |
| Endometrium, other cancers | 4 |
| Ovary, serous malignant cancer | 32 |
| Ovary, mucinous malignant cancer | 4 |
| Ovary, endometrioid malignant cancer | 4 |
| Ovary, mixed mesodermal cancer | 4 |
| Ovary, other cancers | 9 |
| Total parallel serum and urine samples | 112 |

Collection and Preservation of Blood and Urine

Blood samples were collected in ethylenediamine tetraacetic acid tubes. The tubes were centrifuged and plasma removed. Urines were collected and frozen within 5 to 10 minutes. To prevent degradation or cleavage of molecules by hydrolases in urine, preservative was added to samples before thawing. The preservative was used at a dilution of 1:40 and contained 1M Tris-HCL, pH 8.0 (to adjust pH, limit glycosidase activity and the dissociation of hCG), 10 mM disodium ethylenediamine tetraacetic acid (inhibits divalent cation-requiring enzymes), 2 mM phenanthroline (thermolysin inhibitor), 2 mM iodoacetic acid (sulfhydryl protease inhibitor), 5 mg/L pepstatin A (acid protease inhibitor), 5 mg/L leupeptin A (inhibits leucine aminopeptidases), 5 mg/L alpha-1-antitrypsin (serine protease inhibitor) and 0.4% sodium azide (antibacterial). That the pH of urines was in the range 7.3-7.7 was checked with ColorpHast pH 5-10 dip sticks. If needed, additional preservative was added to achieve this pH range. Urines were centrifuged at 2,000 x g to remove debris.

Assays

Urine creatinine levels were determined spectrometrically using Sigma Diagnostics kit No. 555 and the kinetic alkaline picrate procedure. Plasma CA 125 and LASA levels were determined using methods described in Schwartz, P. E., Chambers, S. K., Chambers, J. T., Gutmann, J., Katopodis, N., and Foemmel, R., "Circulating Tumor Markers in the Monitoring of Gynecologic Malignancies", Cancer, 60, 353-361 (1987).

Urine UGF level was determined by immunoradiometric assay methods described in L. A. Cole, Y. Wang, M. Elliott, M. Latif, J. T. Chambers, S. K. Chambers and P. E. Schwartz, "Urinary Human Chorionic Gonadropin Free beta-Subunit and beta-Core Fragment: A New Marker of Gynecologic Cancers", Cancer Res. 48. 1356-1360. (1988).

Nunc Maxisorp tubes were coated with the monoclonal antibody B204 (immunogen: hCG beta-subunit core fragment) (Krichevsky, A., Armstrong, E., Birken, S., Lutbader, J. W., Bikel, K., Silverberg, S., and Canfield, R., "Preparation and Characterization of Antibodies to the Urinary beta Core Fragment of Human Chorionic Gonadotropin", Endocrinology, in press). Urine was placed in tubes and UGF extracted during an overnight incubation. Urine was aspirated, tubes washed, and $^{125}$I- monoclonal antibody HC0514 (immunogen hCG from Hybritech, Inc.) was added. After a further overnight incubation at 4° C., tracer antibody was aspirated, tubes washed and radioactivity was determined. A linear relationship was found between the radioactivity (less than 0 ng/ml standard) and the concentration of hCG free beta-subunit or beta-subunit core fragment. Slope and intercept were determined and a linear regression was used to calculate concentration in experimental tubes from radioactivity. The sensitivity of the assay (concentration different from 0 ng/ml standard with 95% confidence in Student's test) was approximately 0.1 ng/ml. Standard curves in this assay from hCG free beta-subunit, asialo free beta-subunit and core fragment overlapped suggested equal-molar measurement of the three components of UGF. The concentration of cross-reacting hCG or luteinizing hormone required to achieve 50% maximal binding in this assay was 13 times and 350 times, respectively, that of UGF.

Results

UGF levels were measured in 67 control urines (breakdown in Table 1). An average level of 0.13 ng/ml was detected. A cut-off level of 0.2 ng/ml was selected. Six of the 67 control samples (8.9%) exceeded this value. UGF levels were measured in the urines of 112 women with active gynecologic cancers (breakdown by disease in Table 1). Positive levels (exceeding 0.2 ng/ml cut-off) were detected in 72 (64%) samples (Table 2) hereinbelow:

TABLE 2

UGF in Urines of Healthy Subjects and Cancer Patients

| DIAGNOSIS | ELEVATED UGF LEVELS (0.2 ng/ml[a]) | |
|---|---|---|
| | PROPORTION | AVERAGE LEVEL NG/ML |
| CERVICAL CANCER | | |
| Early (stage I[b]) | 8/17 (47%) | 0.73 |
| Advanced (stage II-IV) | 5/9 (56%) | 1.5 |
| Recurrence | 6/6 (100%) | 1.6 |
| All (average stage 1.6) | 19/32 (59%) | 1.2 |
| ENDOMETRIAL CANCER | | |
| Early (stage I) | 3/12 (25%) | 0.37 |
| Advanced (stage II-IV) | 8/9 (89%) | 2.4 |
| Recurrence | 5/6 (84%) | 1.0 |
| All (average stage 1.7) | 16/32 (59%) | 1.6 |
| OVARIAN CANCER | | |
| Early (stage I) | Not available | |
| Advanced (stage II-IV) | 31/43 (72%) | 2.3[c] |
| Recurrence | 6/10 (60%) | 1.6 |
| All (average stage 3.0) | 37/53 (70%) | 2.2 |
| ALL | 72/112 (64%) | 1.8 |
| CONTROL POPULATION (healthy women, 45 age 50, 22 age 50) | 6/67 (9%) | .49 |

[a]Optimal cut-off considering mean UFG level 0.13 ng/ml in 67 control urines.
[b]FIGO (International Federation of Gynecologists and obstetricians);
[c]Stage II = 1.1 ng/ml. III = 1.9 ng/ml, IV = 3.9 ng/ml In the cancer group, mean age 58, 58% of those under 40 years old, 66% of those 41-60, and 65% of those over 60 had positive UGF levels. These values suggested a lack of a correlation between age and sensitivity ($r^2=0.73$ in an age vs. sensitivity regression analysis). While the average UGF level was 1.8 ng/ml in the cancer patients, it averaged 0.5 ng/ml in the 6 false-positive control urines. The sensitivity of UGF was 59% in cervical, 59% in endometrial and 70% in ovarian cancer patients. The average stage of cervical and endometrial cancer was 1.6 and 1.7, respectively, but 3.0 in ovarian cancer patients. A linear relationship ($r^2=0.90$) was observed between stages (I, II, III and IV), regardless of disease, and sensitivity (38%, 68%, 68% and 91% respectively). By linear regression a sensitivity of 52%, 54% and 74% respectively for cervical, endometrial and ovarian cancer would be predicted from an average stage. These numbers are similar to actual figures (59%, 59% and 70%), suggesting a common sensitivity of UGF for all 3 cancers. The average level of UGF in cervical, endometrial and ovarian cancer increased with the stage of disease. Overall an average level of 0.60, 1.8, 1.8 and 3.5 ng/ml was detected in patients with stage I-IV disease respectively ($r^2=0.89$). By linear regression, the average level predicted for cervical endometrial and ovarian cancer was 1.1, 1.2 and 2.4 ng/ml, respectively. Observed levels were similar, 1.2, 1.6 and 2.2 ng/ml, suggesting a similar range of UGF levels in patients with either of the three cancers.

Creatinine levels were measured in all spot urines. Levels ranged from 0.03 to 3.5 mg/ml, and averaged 0.80 mg/ml in control and 0.83 mg/ml in cancer samples. The less concentrated urines (creatinine <0.5 mg/ml) were all from subjects receiving continuous intravascular fluids or were afternoon samples; and the more concentrated (creatinine >0.5 mg/ml) were from first morning samples (average level 1.0 mg/ml). Limiting the study to the 75 samples with creatinine values >0.5 mg/ml, morning urines, raised the sensitivity of UGF to 73%, 65%, and 83% respectively for cervical, endometrial and ovarian cancers (Table 3). The sensitivity, specificity and predictive value of UGF and serum tumor markers was compared (Table 3 hereinbelow).

TABLE 3

Sensitivity, Specificity and Predictive Value of Markers in Gynecologic Cancer[a]

| PRIMARY SITE | ASSAY | SENSITIVITY (%) | SPECIFICITY[b] (%) | PV +[c] (%) | PV −[d] (%) | E[e] (%) |
|---|---|---|---|---|---|---|
| Cervix | UGF | 59 | 91 | 87 | 69 | 75 |
| Endometrium | UGF | 59 | 91 | 87 | 69 | 75 |
| Ovary | UGF | 70 | 91 | 89 | 75 | 81 |
| All | UGF | 64 | 91 | 88 | 72 | 78 |
| Cervix | UGF, C > 0.5[f] | 73 | 89 | 87 | 77 | 81 |
| Endometrium | UGF, C > 0.5 | 65 | 89 | 86 | 72 | 77 |
| Ovary | UGF, C > 0.5 | 83 | 89 | 88 | 84 | 86 |
| All | UGF, C > 0.5 | 76 | 89 | 87 | 79 | 83 |
| Cervix | LASA | 32 | 94 | 84 | 58 | 63 |
| Endometrium | LASA | 50 | 94 | 89 | 65 | 72 |
| Ovary | LASA | 49 | 94 | 89 | 65 | 72 |
| All | LASA | 45 | 94 | 88 | 63 | 70 |
| Endometrium | CA 125 | 61 | 92 | 88 | 70 | 77 |
| Ovary | CA 125 | 65 | 92 | 89 | 72 | 79 |
| All[g] | CA 125 | 62 | 92 | 89 | 71 | 77 |

[a]UGF cut-off value as in Table 2; LASA, mean level 18 mg/dl in 70 control serum samples, selected cut-off value 24 ng/ml; CA 125, mean level 18 U/ml in 70 control serum samples, selected cut-off value 35 U/ml.
[b]Specificity = (true negatives/total control samples) × 100
[c]Predictive value positive = (true positives/true + false positives) × 100
[d]Predictive value negative = (true negatives/true + false negatives) × 100
[e]Efficiency = (true positive + negatives/total positives + negatives) ÷ 100
[f]UGF values from urines with creatine level > 0.5 mg/ml
[g]Endometrium and ovary only While the specificity of UGF (samples with creatinine >0.5 mg/ml) was slightly lower than CA 125 and LASA (89% vs. 92% and 94%), the sensitivity was distinctly higher for all cancers. Positive UGF levels were found in 73% of cervical (vs. LASA in 32%), 65% of endometrial (vs. CA 125 in 61%) and 83% of ovarian (vs. CA 125 in 65%) cancer patients.

All patients with elevated LASA or CA 125 levels in cervical or endometrial cancer also had positive UGF levels, so that combining other markers with UGF did not improve sensitivity. UGF, however, was detected in over three quarters of those with ovarian cancer and negative CA 125 levels (<35 U/ml), including 4 or 5 patients with serous disease. Whereas the ovarian cancer sensitivity of UGF (samples with creatinine >0.5 mg/ml) alone is 83%, and of CA 125 alone is 65%, that of either marker in the same patient is 92%.

If the cut-off value of UGF is raised from 0.2 to 0.5 ng/ml, for cancer screening applications, the specificity rises to 96%. Although the overall sensitivity drops (Table 4 hereinbelow), the positive predictive value becomes 94%, higher than that of serum markers (Table 3), and possibly sufficient for screening applications.

TABLE 4

UGF in Screening for Gynecologic Cancer[a]

| PRIMARY SITE | SENSITIVITY (%) | SPECIFICITY (%) | PV + (%) |
|---|---|---|---|
| Cervix | 64 | 96 | 94 |
| Endometrium | 47 | 96 | 94 |
| Ovary | 69 | 96 | 95 |
| All | 63 | 96 | 94 |

[a]Using a cut-off of 0.5 ng/ml in urines with 0.5 mg/ml creatinine

Example 2: Serial Studies Correlating UGF, CA 125 and LASA Levels With Changing Clinical Status in Women Undergoing Therapy for Cervical, Endometrial or Ovarian Cancer Patients and Preservation of Urines Parallel urine and blood samples were collected from patients with gynecologic cancer undergoing chemo- or radiotherapy. Samples were also collected from women undergoing surgery for gynecologic cancer. Blood samples were collected in ethylenediamine tetraacetic acid tubes. The tubes were centrifuged and plasma was removed. Urines were frozen within 5 to 10 minutes of collection. As described in Example 1, preservatives were added to prevent degradation or cleavage of molecules by urinary hydrolases. Urines were centrifuged to remove debris before assay.

Assays

Plasma CA 125 and LASA levels were determined using methods described in P. E. Schwartz, S. K. Chambers, J. T. Chambers, J. Gutmann, N. Katopodis and R. S. Foemmel, "Circulating Tumor Markers in the Monitoring of Gynecologic Malignancies", *Cancer*, 60, 353–361, (1987). UGF was measured by immunoradiometric assay using antibody B204 (immunogen hCG beta-subunit core fragment) to extract and radiolabeled antibody HC0514 (immunogen hCG B-subunit, from Hybritech Inc., CA) to detect substrate. The UGF assay procedure is described in Example 1 hereinabove.

Results

Over a 7 month period, UGF levels were monitored in serial urines from 28 woman undergoing therapy for cervical, ovarian or endometrial cancer. Changes in UGF levels and clinical status were compared. UGF levels correlated with changing clinical status in 23 of the 28 patients, as was judged by a continual increase in levels in constantly progressive disease, the converse in regressing cancer, or up to 40% variation in levels in the patients with the stable mass (Table 5) hereinbelow:

TABLE 5

Correlation of Changes in Clinical Status With Levels of UGF, CA 125 and LASA in Serial Samples from Patients Receiving Therapy for Active Cancer

| PATIENT | TISSUE | STAGE[a] | THERAPY[b] | COURSE[c] | CORRELATES WITH CLINICAL STATUS[d] | | |
|---|---|---|---|---|---|---|---|
| | | | | | UGF | CA 125 | LASA |
| CERVICAL CANCER | | | | | | | |
| 1 | Squamous | I | Surg | Reg | No | No | No |
| 2 | Squamous | R | Chemo | Pro | Yes | Yes | No |
| 3 | Squamous | R | Chemo | Pro, Stable | Yes | Yes | No |
| | | | | Summary | 2/3 | 2/3 | 0/3 |
| ENDOMETRIAL CANCER | | | | | | | |
| 4 | Adenocarcinoma | I | Chemo | Pro, Reg | Yes | Yes | Yes |

TABLE 5-continued

Correlation of Changes in Clinical Status With Levels of UGF, CA 125 and LASA in Serial Samples from Patients Receiving Therapy for Active Cancer

| PATIENT | TISSUE | STAGE[a] | THERAPY[b] | COURSE[c] | CORRELATES WITH CLINICAL STATUS[d] | | |
|---|---|---|---|---|---|---|---|
| | | | | | UGF | CA 125 | LASA |
| 5 | Adenocarcinoma | R | Chemo | Reg, NED | Yes | No | No |
| 6 | Adenocarcinoma | R | Chemo | Slowly Pro | Yes | No | No |
| 7 | Adenocarcinoma | R | Chemo | Pro | Yes | Yes | Yes |
| 8 | Adenocarcinoma | I | Surg + Chemo | Reg, Pro | Yes | Yes | No |
| 9 | Adenocarcinoma | III | Surg | Reg | Yes | Not available | |
| 10 | Adenocarcinoma | R | Chemo | Pro | Yes | No | Yes |
| 11 | Papillary Serous Carcinoma | R | Chemo + RT | Reg, Pro | Yes | No | No |
| | | | | Summary | 8/8 | 3/7 | 3/7 |
| OVARIAN CANCER | | | | | | | |
| 12 | Serous | III | Chemo | Reg | Yes | No | No |
| 13 | Serous | IV | Chemo | Reg | Yes | Yes | Yes |
| 14 | Serous | III | Chemo | Pro | Yes | Yes | No |
| 15 | Serous | III | Surg | Reg, NED | No | Yes | No |
| 16 | Serous | R | None | Pro | Yes | Yes | Yes |
| 17 | Serous | II | Chemo | Reg | Yes | Yes | Yes |
| 18 | Serous | IV | Chemo | Pro, Stable | No | Yes | No |
| 19 | Serous | III | Chemo | Pro, Reg | Yes | Yes | No |
| 20 | Serous | R | Surg | NED[e] | Yes | No[f] | No[f] |
| 21 | Serous | III | Chemo | Stable, Pro | Yes | Yes | No |
| 22 | Serous | III | Chemo + Surg | Reg, NED | Yes | No | Yes |
| 23 | Serous | III | Chemo | Pro | No | Yes | Yes |
| 24 | Serous | III | Chemo | Stable | No | No | No |
| 25 | Serous | III | Surg + Chemo | Pro | Yes | Yes | Partly |
| | | | | Summary | 10/14 | 16/27 | 5/13 |
| 26 | Mucinous | III | Chemo | Stable | Yes | Yes | No |
| 27 | Endometrioid | R | Chemo | Reg, Stable | Yes | No | No |
| 28 | Teratoma | III | Chemo | Reg | Yes | No | Yes |
| | | | | Summary | 3/3 | 1/3 | 1/3 |
| | | | | OVERALL SUMMARY | 23/28 (82%) | 16/27 (59%) | 9/26 (35%) |

[a]FIGO (International Federation of Gynecologists and Obstetricians); R, reccurrent cancer
[b]Treatment during the study period: Chemo, chemotherapy; Surg, surgery; RT, radiation therapy
[c]As suggested by clinical status: Pro, progressive cancer or enlarging mass; Reg, regressing cancer or dimishing mass; NED, no evidence of disease; multiple notations linked by comma indicated change in course of cancer during the study period
[d]Correlation was judged as a continuous increase in marker level in patients with monthly clinical evaluations that consistantly indicate progressive disease, or the converse with regressing cancer, or appropriately increasing and decreasing levels with tumors that follow a changing course
[e]In fifth month of study (FIG. 3), second-look surgery revealed occult intraperitoneal metastases
[f]All values in normal range thus failing to detect occult cancer identified by second-look surgery.

Figure 3:
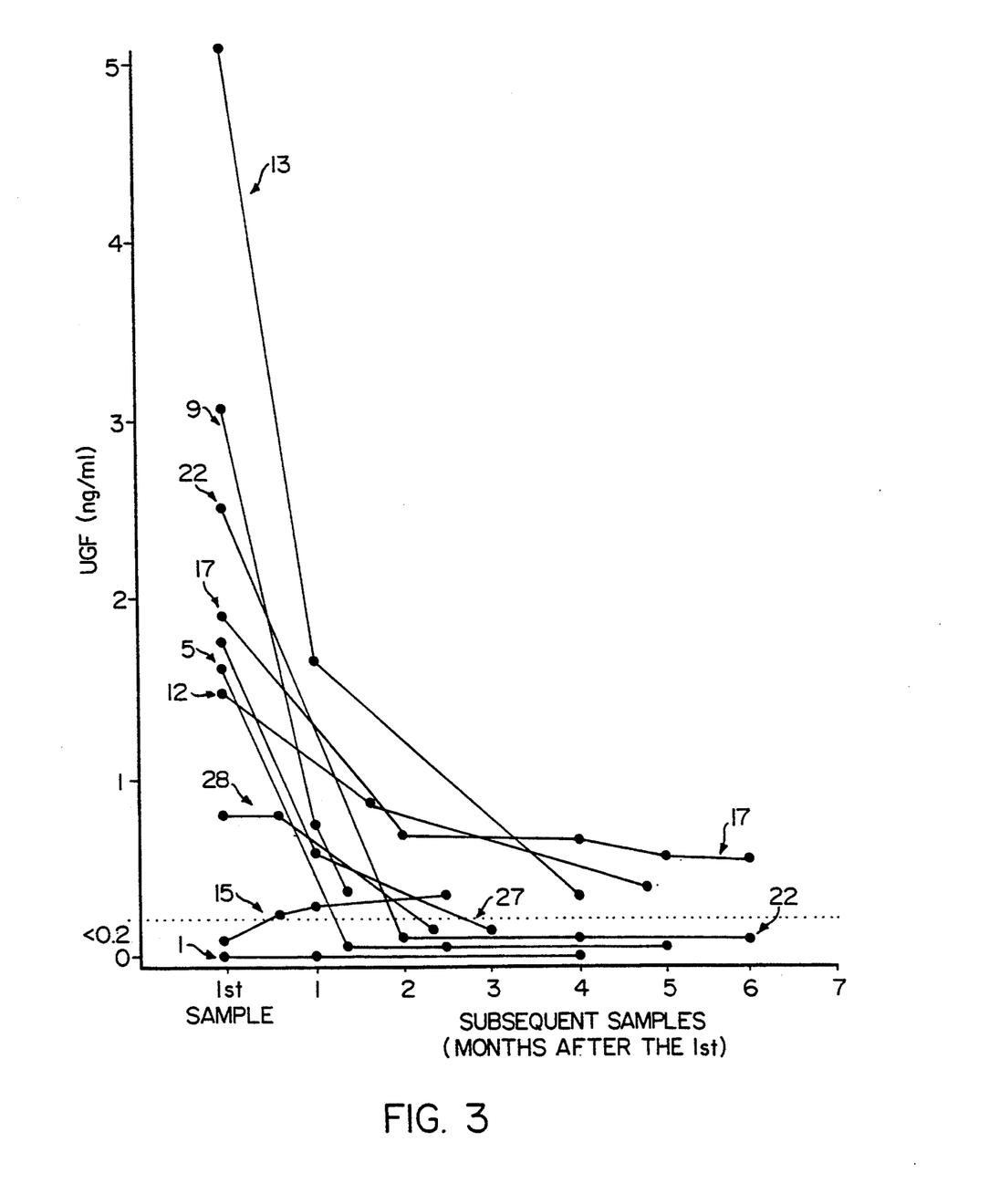
FIG. 3 is a plot depicting UGF levels in women undergoing therapy for gynecologic cancer. Values are from 8 women with a stable or varied course. The patient number, beside each line, references the clinical evaluations in Table 5.

The 23 patients were comprised of 2 of 3 patients with cervical, 8 of 8 patients with endometrial, and 13 of 17 patient with ovarian malignancies. A direct correlation of UGF levels with clinical status was observed in 8 of 10 patients with successful therapy and continuously diminishing tumor mass (FIG. 1), and in 8 or 10 patients with progressive disease (FIG. 2). UGF levels also are correlated with clinical status in 7 of 8 patients with a stable tumor (patient 24 and 26), or with cancer changing course in the study period (patient 4, 8, 11, 19 and 21) or with no evidence of disease (Patient 20) but having cancer as demonstrated by pathology at second-look surgery (FIG. 3). The 5 patients with UGF levels discordant with clinical status included 4 with normal range UGF values ( 0.2 ng/ml) throughout the study period, and 1 (Patient 15) with levels increasing from negative ( 0.2 ng/ml) pre-surgery to low positive (0.5 ng/ml) in the ensuing months with no disease clinically evident.

The efficacy of UGF in monitoring patients with gynecologic cancers was compared with that of CA 125 and LASA (Table 5). Overall, changes in UGF levels correlated with clinical course in 82%, CA 125 in 59% and LASA in 35% of patients. CA 125 levels correlated with clinical course in 10 of 14 (71%) patients with serous ovarian cancer, as did UGF. CA 125 levels, however, were only concordant with clinical course in 1 of 3 patients with non-serous disease, compared with each of 3 for UGF. Using either CA 125 or UGF, levels of one or both markers correlated with the clinical course in 2 of 3 patients with cervical, 8 of 8 patients with endometrial and 16 of 17 patients with ovarian cancer. Using either CA 125 or UGF the course of therapy for gynecologic cancer was accurately monitored in 26 of 28 patients ( 93 % ).

EXAMPLE 3:

The following Table 6 represents the results of clinical testing demonstrating the high specificity of the invention as a test for cancer, i.e., it does not pick up benign diseases unlike other tests.

TABLE 6

Sensitivity of UGF (Beta Core Fragment) for Control Urines Elevated UGF Levels (>0.2 ng/ml)

| Premenopause | | |
|---|---|---|
| No history of cancer | | 0 of 57 |
| Postmenopause | | |
| No history of cancer | | 2 of 60   3.3% |
| On estrogen | 0 of 16 | |
| Not on estrogen | 0 of 13 | |
| Not known | 2 of 31 | |
| Benign gynecologic disease | | 1 of 70   1.4% |
| Endometriosis | 0 of 10 | (8 of 10 had elevated levels of CA125) |
| Condyloma | 0 of 13 | |
| Ovarian cyst | 1 of 11 | |

TABLE 6-continued

Sensitivity of UGF (Beta Core Fragment) for
Control Urines
Elevated UGF Levels (>0.2 ng/ml)

| | | |
|---|---|---|
| Myoma | 0 of 10 | |
| Other | 0 of 26 | |
| No evidence of disease 3 years post therapy for gynecologic cancer | | 0 of 67 |
| | | 3 of 254  1.1% |

It will be appreciated that the instant specification are set forth by way of illustration and not limitation, and that various modifications and changes may be made without departing from the spirit and scope of the present invention.

What is claimed is:

1. A method for detecting the progression or regression of a gynecologic cancer in a female, said cancer selected from the group consisting of cervical cancer, ovarian cancer, endometrial cancer, uterine cancer and vulva cancer, the method comprising:
   (a) taking a first measurement of an amount of human chorionic gonadotropin beta-subunit core fragment in a bodily non-blood fluid sample from a female known to be suffering from a said gynecologic cancer,
   (b) subsequent to step (a), taking one or more further measurements of human chorionic gonadotropin beta-subunit core fragment from a bodily non-blood fluid sample from said female, and
   (c) comparing the first measurement to said one or more further measurements to ascertain if the human chorionic gonadotropin beta-subunit core fragment is increasing or decreasing, as an indication that said gynecologic cancer is respectively progressing or regressing.

2. A method according to claim 1, wherein the sample is selected from the group consisting of urine, ascites fluid, spinal fluid, biopsy material, saliva and vaginal fluid.

3. A method according to claim 1, wherein the fluid is urine.

4. A method for detecting the presence of a gynecologic cancer in a female, said cancer selected from the group consisting of cervical cancer, ovarian cancer, endometrial cancer, uterine cancer and vulva cancer, the method comprising:
   (a) assaying a plasma or tissue sample from the patient for the presence of CA 125, and at or about the same time,
   (b) assaying a bodily non-blood sample from said patient for the presence of human chorionic gonadotropin beta-subunit core fragment, wherein the detection of both CA 125 and human chorionic gonadotropin beta-subunit core fragment is an indication of the presence of a gynecological cancer in the female.

5. A method according to claim 4, wherein the sample for (b) is a urine sample.

6. A method according to claim 4, wherein the sample for (a) is a plasma sample.

7. A method for detecting the presence of a recurrence of a gynecologic cancer in a female patient before the patient has clinical signs or symptoms, said cancer selected from the group consisting of cervical cancer, ovarian cancer, endometrial cancer, uterine cancer and vulva cancer, the method comprising:
   (a) assaying a plasma or tissue sample from the patient for the presence of CA 125, and at or about the same time,
   (b) assaying a bodily non-blood sample from said patient for the presence of human chorionic gonadotropin beta-subunit core fragment, wherein the detection of both CA 125 and human chorionic gonadotropin beta-subunit core fragment is an indication of the presence or recurrence of a gynecological cancer in the female.

8. A method to screen a female patient having a high risk of developing ovarian cancer comprising:
   (a) assaying a plasma or tissue sample from the patient for the presence of CA 125, and at or about the same time,
   (b) assaying a bodily non-blood sample from said patient for the presence of human chorionic gonadotropin beta-subunit core fragment, wherein the detection of both CA 125 and human chorionic gonadotropin beta-subunit core fragment is an indication that the female patient has a high risk of developing ovarian cancer.

9. A method for distinguishing a benign from a malignant pelvic mass, growth or cyst in a female patient comprising:
   (a) assaying a plasma or a tissue sample from the patient for the presence of CA 125, and at or about the same time,
   (b) assaying a bodily non-blood sample from said patient for the presence of human chorionic gonadotropin beta-subunit core fragment, wherein the detection of both CA 125 and human chorionic gonadotropin beta-subunit core fragment is an indication of a malignant pelvic mass, growth or cyst in the female patient.

* * * * *